United States Patent
Backus et al.

(10) Patent No.: US 6,280,930 B1
(45) Date of Patent: *Aug. 28, 2001

(54) AMPLIFYING AND DETECTING TARGET NUCLEIC ACIDS USING A POST AMPLIFICATION INCUBATION STEP

(75) Inventors: John W. Backus, Pittsford; Marcia L. Kramer; Joseph Falvo, both of Rochester, all of NY (US)

(73) Assignee: Johnson & Johnson Clinical Diagnostics, Inc., Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/845,739

(22) Filed: Apr. 25, 1997

Related U.S. Application Data

(63) Continuation-in-part of application No. 08/613,571, filed on Mar. 11, 1996, now abandoned.

(51) Int. Cl.$^7$ ............... C12Q 1/68; C12P 19/34
(52) U.S. Cl. ............... 435/6; 435/91.2
(58) Field of Search ............. 435/6, 91.2, 91.21

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,210,015 | 5/1993 | Gelfand et al. | 435/6 |
| 5,229,297 | * 7/1993 | Schnipelsky et al. | 438/94 |
| 5,635,347 | * 6/1997 | Link et al. | 435/6 |
| 5,645,801 | * 7/1997 | Bouma et al. | 422/68.1 |

FOREIGN PATENT DOCUMENTS

| | | | |
|---|---|---|---|
| 297 379 B1 | 8/1992 | (EP) | 1/68 |

OTHER PUBLICATIONS

Kaluz et al. Nucl. Acids Res (1991) 19(14): 4012.*

* cited by examiner

*Primary Examiner*—Lisa B. Arthur
(74) *Attorney, Agent, or Firm*—Catherine Kurtz Gowen

(57) ABSTRACT

The present invention relates to a method for amplifying and detecting a target nucleic acid. The method comprising contacting a sample suspected of containing the target nucleic acid with a thermostable DNA polymerase and two primers that are substantially complementary to the target nucleic acid, under conditions such that the target nucleic acid is amplified. The amplified target nucleic acids are then denatured to form single stranded nucleic acids. Following amplification, the sample is subject to a pre-detection incubation step. The sample is incubated for between 1 second and 30 minutes at between 95° C. and 120° C. to inactivate said polymerization agent. Finally, the presence or absence of the amplified target nucleic acids is determined. Preferably, amplification, incubation and detection are carried out in a closed reaction vessel.

21 Claims, No Drawings

AMPLIFYING AND DETECTING TARGET NUCLEIC ACIDS USING A POST AMPLIFICATION INCUBATION STEP

BACKGROUND INFORMATION

This is a continuation-in-part of application Ser. No. 08/613,571, filed on Mar. 11, 1996, now abandoned the entire contents of which are hereby incorporated by reference.

FIELD OF THE INVENTION

The present invention relates to a method for amplifying and detecting target nucleic acids. In particular, it relates to improved methods of detecting amplified nucleic acid products. The present invention can be used in various medical and research studies, forensic investigations, and diagnostic procedures, such as for the detection of genetic disorders or infectious diseases.

BACKGROUND OF THE INVENTION

Technology to detect minute quantities of nucleic acids has advanced rapidly over the last two decades including the development of highly sophisticated hybridization assays using probes in amplification techniques such as polymerase chain reaction (PCR). Researchers have readily recognized the value of such technology to detect diseases and genetic features in human and animal test specimens. The use of primers and probes in the amplification and detection of nucleic acids is based upon the concept of complementarity, that is, the bonding of two strands of a nucleic acid by hydrogen bonds between complementary nucleotides (which are known as nucleotide pairs).

Much research has been carried out to find ways to amplify and detect small quantities of DNA. Various procedures are known and have been used to amplify or greatly multiply the number of nucleic acids in a specimen for detection. Such amplification techniques include PCR, ligase chain reaction (LCR), and branched DNA.

PCR is the most well known of these amplification methods. Details of PCR are well described in the art, including, for example, U.S. Pat. No. 4,638,195 (Mullis et al.), U.S. Pat. No. 4,683,202 (Mullis), and U.S. Pat. No. 4,965,188 (Mullis et al.). Without going into extensive detail, PCR involves hybridizing primers to the strands of a target nucleic acid in the presence of polymerization agent (such as a DNA polymerase) and deoxyribonucleoside triphosphates under the appropriate conditions. The result is the generation of primer extension products along the templates, the products having added thereto nucleotides that are complementary to the templates.

Once the primer extension products are denatured and one copy of the templates has been prepared, the cycle of priming, extending and denaturation can be carried out as many times as desired to provide an exponential increase in the amount of nucleic acid that has the same sequence as the target nucleic acid. In effect, the target nucleic acid is duplicated (or "amplified") many times so that it is more easily detected. Once the target nucleic acid has been sufficiently amplified, various detection procedures can be used to detect, qualitatively and/or quantitatively, the presence of the target.

Once the target nucleic acid has been sufficiently amplified, various detection procedures can be used to detect its presence. A standard detection method used to detect PCR products has been ethidium bromide stained agarose gels. Use of ethidium bromide stained gels, however, has several disadvantages including, for example, relatively poor sensitivity and specificity.

Improved methods of detecting PCR products that eliminate the use of radiolabels and electrophoresis have been developed. These nonisotopic oligonucleotide capture detection methods rely on specific hybridization to probes and enzymatic signal generation. Such nonisotopic oligonucleotide capture detection methods, also known as reverse dot blot detection, are described in U.S. Pat. No. 5,229,297 (Schnepilsky et al.), U.S. Pat. No. 5,328,825 (Warren et al.), and U.S. Pat. No. 5,422,271 (Chen et al.). Such a method is also described in Findlay et al., Clinical Chemistry, 39:1927–1933 (1993).

These nonisotopic detection methods have higher sensitivity and specificity than ethidium bromide staining detection and avoid the use of radioactivity. The methods operate by either carrying out amplification with biotinylated primer(s) or using a biotinylated probe to detect the amplified nucleic acids. Biotinylated products or probes are subsequently reacted with an avidin or streptavidin conjugated enzyme such as horseradish peroxidase (HRP). A dye precursor (or light generating signal reagent) can then be brought into contact with the enzyme and be converted into a dye (luminescence) thereby generating a detectable signal.

Nonisotopic oligonucleotide capture detection methods are not, however, without their own drawbacks. If nonisotopic oligonucleotide capture detection is carried out utilizing standard PCR denaturation conditions (95° C.) to denature concentrated or minimally diluted amplified nucleic acid products, the enzymes utilized to carry out the amplification reaction, such as thermostable polymerases or DNA ligases, will still be present and active. The presence of such active enzymes during detection results in competition between and binding of the probe to the denatured amplification product. Such competition can reduce the amount of amplified nucleic acid products bound to probe and therefor, the detection signal.

One solution to this problem has been to add high levels of ethylenediamine tetraacetic acid (EDTA), a chelator of $Mg^{++}$, to the PCR amplification mixture after amplification has been carried out but prior to detection.

EDTA is able to inhibit many enzymes requiring $Mg^{++}$ for activity including DNA polymerases and DNA ligases. Use of EDTA, however, adds an additional step to the PCR amplification and detection process. In addition, use of EDTA requires opening up the reaction vessel to add the EDTA. As those skilled in the art are aware, opening the reaction vessel is to be avoided because of contamination concerns.

Thus, blocking the amplification process during detection through the addition of EDTA or other such enzyme inhibitors is not desired. Rather, it is desirable to have a method of inactivating the amplification enzymes prior to detection without the increased risk of contamination.

SUMMARY OF THE INVENTION

It is an object of the present invention to overcome the problems noted above by using a post amplification incubation step prior to detection to inactivate the amplification enzymes.

In one embodiment, the present invention relates to a method for amplifying and detecting a target nucleic acid in an enclosed reaction vessel comprising:

(i) contacting a sample suspected of containing the target nucleic acid with at least two oligonucleotides and a thermostable amplification enzyme, wherein the oligonucleotides are substantially complementary to a portion of the target nucleic acid, under conditions such that the target nucleic acid is amplifiable;

(ii) amplifying the target nucleic acid;

(iii) denaturing amplified target nucleic acids to form single stranded nucleic acids;

(iv) incubating the sample for between 1 second and 30 minutes at between 95° C. and 120° C., as a post amplification incubation step to inactivate the thermostable amplification enzyme; and (v) detecting the presence or absence of the amplified target nucleic acids, wherein the reaction vessel remains closed.

In a further embodiment, the present invention relates to a method for amplifying and detecting a target nucleic acid in a reaction vessel comprising:

(i) contacting a sample suspected of containing the target nucleic acid with four different nucleoside triphosphates, a thermostable DNA polymerase, and at least two primers, wherein the primers are substantially complementary to the target nucleic acid, under conditions such that the target nucleic acid is amplifiable;

(ii) amplifying the target nucleic acid;

(iii) denaturing amplified target nucleic acids to form single stranded nucleic acids;

(iv) incubating the sample for between 1 second and 30 minutes at between 95° C. and 120° C., as a post amplification incubation step to inactivate the polymerization agent; and (v) detecting the presence or absence of the amplified target nucleic acids, wherein the reaction vessel remains closed during amplification and detection.

In another embodiment, the present invention relates to a method for amplifying and detecting a target nucleic acid in a reaction vessel comprising:

(i) contacting a sample suspected of containing target nucleic acid with four different nucleoside triphosphates, a thermostable DNA polymerase, and at least two primers, wherein at least one of the primers is labeled with biotin and all primers are substantially complementary to the target nucleic acid, under conditions such that the target nucleic acid is amplifiable;

(ii) amplifying the target nucleic acid;

(iii) incubating the sample for between 0.5 minutes and 5 minutes at about 105° C., as a post amplification incubation step to inactivate the polymerase; and (iv) detecting the presence or absence of the biotinylated amplified target nucleic acids by reacting the biotinylated amplified target nucleic acids with a streptavidin-enzyme conjugate, followed by reaction of the enzyme with a substrate reagent to produce a detectable calorimetric or chemiluminescent signal, wherein the reaction vessel remains closed.

Various other objects and advantages of the present invention will be apparent from the following description of the invention.

DETAILED DESCRIPTION OF THE INVENTION

The general principles and condition for amplification and detection of nucleic acids using polymerase chain reaction are quite well known, the details of which are provided in numerous references including U.S. Pat. No. 4,683,195 (Mullis et al.), U.S. Pat. No. 4,683,202 (Mullis), and U.S. Pat. No. 4,965,188 (Mullis et al.), all of which are incorporated herein by reference. Thus, in view of the teaching in the art and the specific teaching provided herein, a worker skilled in the art should have no difficulty in practicing the present invention by adding a post amplification incubation step to inactivate the amplification enzymes prior to product detection as taught herein to increase detection sensitivity.

Other amplification and detection procedures employing thermostable enzymes can also be used in the practice of this invention. The present invention provides for a post amplification, pre-detection incubation step that inactivates the thermostable enzyme(s) used during amplification. Thus, the present invention is suitable for use with any amplification method employing a thermostable enzyme. Other thermostable amplification methods include ligase chain reaction (LCR) as described, for example, in EP-A-0 320 308 (published December, 1987) and EP-A-0 439 182 (published January, 1990), and gap LCR as described, for example, in EP-A-O 439 182. Both LCR and gap LCR use a thermostable DNA ligase to ligate adjoining probes thereby creating a complementary nucleic acid sequence.

In LCR target nucleic acids are amplified using 4 oligonucleotide probes and a thermostable DNA ligase. Two of the oligonucleotide probes are complementary to adjacent sites on one strand of the DNA template to be amplified. These probes hybridize to that DNA strand such that a nick is formed between the two probes. The nick is then sealed by a thermostable DNA ligase thereby creating a new strand of DNA complementary to the target. The third and fourth probes are complementary to the second strand of the DNA template and function like the first pair of probes to generate a complementary DNA. The amplified products of LCR can be detected using standard detection methods. The post amplification, pre-detection incubation step of the present invention can be used with LCR to inactivate the DNA ligase prior to detection. Thus, the teachings provided herein would allow one skilled in the art to adapt the post amplification enzyme denaturation step shown for PCR to these other known amplification and detection procedures. The remainder of this disclosure is directed to practicing the invention using PCR for illustrative purposes.

The present invention provides a modification of known methods of PCR in order to improve detection sensitivity. It has been surprisingly discovered in accordance with the present invention that a post amplification, pre-detection incubation step can be used to inactivate the polymerization agent and reduce the competition between binding the probe to the amplified target nucleic acid and the continuing amplification process. This reduced competition increases detection sensitivity. This post amplification, pre-detection incubation step can be incorporated into the amplification and detection process in the absence of a step that opens the reaction vessel, thereby avoiding the exposure of its contents to the environment and subsequent potential contamination.

The present invention is directed towards the amplification and detection of one or more target nucleic acids present in a test specimen. Test specimens can include cellular or viral material, body fluids or other cellular materials containing genetic DNA or RNA that can be detected.

Nucleic acids to be amplified and detected can be obtained from various sources including plasmids and naturally occurring DNA or RNA from any source (such as bacteria, yeast, viruses, plants, higher animals, or humans). It may be extracted from various tissues including but not limited to, blood, peripheral blood mononuclear cells (PBMC), tissue material or other sources known in the art using known procedures. The present invention is particularly useful for the amplification and detection of one or more nucleic acid sequences found in genomic DNA, bacterial DNA, fungal DNA, viral RNA, or DNA or RNA found in bacterial or viral infected cells.

The method described herein can be used to amplify and detect target nucleic acids associated with infectious diseases, genetic disorders, and cellular disorders such as cancer. It may also be used for forensic investigations and DNA typing. It is particularly useful for the detection of infectious agents, such as bacteria and viruses, by detection of nucleic acids associated therewith. It has particular utility when very high sensitivity and/or quantitation is required.

Bacteria that can be detected by the present invention include, but are not limited to, bacteria found in human blood, such as Salmonella species, Streptococcus species, Chlamydia species, Gonococcal species, Mycobacteria species (such as, *Mycobacterium tuberculosis* and *Mycobacterium avium* complex), Mycoplasma species (such as *Mycoplasma Hemophilus influenzae* and *Mycoplasma pneumoniae*), *Legionella pneumophila, Borrelia burgdorferei, Pneumocystis carinii, Clostridium difficile,* Camplyobacteri species, Yersinia species, Shigella species and Listeria species. Viruses that are detectable include, but are not limited to, cytomegalovirus, herpes simplex virus, Epstein Barr virus, human papilloma viruses, influenza viruses, hepatitis viruses, and retroviruses (such as, HTLV-I, HTLV-II, HIV-I and HIV-II). Protozoan parasites, yeasts and molds are also detectable by the present invention. Other detectable species would be readily apparent to one skilled in the art.

A "PCR reagent" refers to any of the reagents considered essential for PCR, namely a set of primers for each target nucleic acid, a DNA polymerase, a DNA polymerase cofactor, and one or more deoxyribonucleoside-5'-triphosphates (dNTP's). Other optional reagents and materials used in PCR are described below.

The term "primer" refers to an oligonucleotide, whether naturally occurring or synthetically produced, that is capable of acting as a point of initiation of synthesis when placed under conditions in which synthesis of a primer extension product complementary to a nucleic acid strand (that is, template) is induced, such conditions include the presence of other PCR reagents, and suitable temperature and pH.

The primers of the present invention are selected to be "substantially complementary" to the specific nucleic acid sequence to be primed and amplified. This means that they must be sufficiently complementary to hybridize with the respective nucleic acid sequences to form the desired hybridized products and then be extendable by a DNA polymerase. Typically, a "substantially complementary" primer will contain at least 70% or more bases which are complementary to the target sequence. More preferably 80% of the bases are complementary, and even more preferably 90% of the bases are complementary. In the most preferred situations, the primers have between 90% and 100% exact complementarity to the target nucleic acid sequence.

The primer is preferably single stranded for maximum efficiency in amplification, but can contain a double stranded region if desired. It must be long enough to prime the synthesis of extension products in the presence of the DNA polymerase. The exact size of each primer will vary depending upon the use contemplated, the concentration and sequence of the primer, the complexity of the targeted sequence, the reaction temperature, and the source of the primer. Generally, the primers used in this invention will have from 12 to 60 nucleotides, and preferably, they have from 16 to 40 nucleotides. More preferably, each primer has from 18 to 35 nucleotides.

Primers useful herein can be prepared using known techniques and equipment, including for example an ABI DNA Synthesizer (available from Applied Biosystems) or a Biosearch 8600 Series or 8800 Series Synthesizer (available from Milligen-Biosearch, Inc.). Procedures for using this equipment are well known and described for example in U.S. Pat. No. 4,965,188 (Gelfand et al.), incorporated herein by reference. Naturally occurring primers isolated from biological sources may also be useful (such as restriction endonuclease digests). A set of at least two primers is generally used for each target nucleic acid. Thus, a plurality of sets of primers can be used simultaneously to amplify a plurality of target nucleic acids.

As used herein, a "probe" is an oligonucleotide which is substantially complementary to a nucleic acid sequence of the target nucleic acid and which is used for detection or capture of the amplified target nucleic acid.

The primers and/or the probes used in the present invention can, optionally, be labeled. Using known methods in the art, the primers and/or probes can be labeled with a specific binding ligand (such as biotin), an enzyme (such as glucose oxidase, peroxidases, uricase, and alkaline phosphatase), radioisotopes, electron-dense reagents, chromogens, fluorogens, phosphorescent moieties or ferritin. Preferably, the label is a specific binding ligand. More preferably, the label is biotin or a derivative thereof, streptavidin or a derivative thereof or a hapten.

Additional PCR reagents necessary for PCR include a DNA polymerase (preferably a thermostable DNA polymerase), a DNA polymerase cofactor and appropriate dNTP's. These reagents can be provided individually, as part of a test kit, or in reagent chambers of test devices.

A DNA polymerase is an enzyme that will add deoxynucleoside monophosphate molecules to the 3'-hydroxy end of the primer in a complex of primer and template, but this addition is in a template dependent manner. Generally, synthesis of extension products proceeds in the 5' to 3' direction of the newly synthesized strand until synthesis is terminated. Useful DNA polymerases include, for example, *E. coli* DNA polymerase I, T4 DNA polymerase, Klenow polymerase, reverse transcriptase and others known in the art. Preferably, the DNA polymerase is thermostable meaning that it is stable to heat and preferentially active at higher temperatures, especially the high temperatures used for priming and extension of DNA strands. More particularly, thermostable DNA polymerases are not substantially inactive at the high temperatures used in polymerase chain reactions as described herein. Such temperatures will vary depending on a number of reaction conditions, including pH, nucleotide composition, length of primers, salt concentration and other conditions known in the art.

A number of thermostable DNA polymerases have been reported in the art, including those mentioned in detail in U.S. Pat. No. 4,965,188 (Gelfand et al.) and U.S. Pat. No. 4,889,818 (Gelfand et al.), both incorporated herein by reference. Particularly useful polymerases are those obtained from various Thermus bacterial species, such as *Thermus aquaticus, Thermus thermophilus, Thermus filiformis,* and *Thermus flavus.* Other useful thermostable polymerases are obtained from various microbial sources including *Thermococcus literalis, Pyrococcus furiosus,* Thermotoga sp. and those described in WO-A-89/06691

(published Jul. 27, 1989). Some useful thermostable polymerases are commercially available, such as, AppliTaq®, Tth, and UlTma™ from Perkin Elmer, Pfu from Stratagene, and Vent and Deep-Vent from New England Biolabs. A number of techniques are also known for isolating naturally-occurring polymerases from organisms, and for producing genetically engineered enzymes using recombinant techniques.

A DNA polymerase cofactor refers to a nonprotein compound on which the enzyme depends for activity. Thus, the enzyme is catalytically inactive without the presence of cofactor. A number of materials are known cofactors including, but not limited to, manganese and magnesium salts, such as chlorides, sulfates, acetates and fatty acids salts. Magnesium chlorides and sulfates are preferred.

Also needed for PCR are two or more deoxyribonucleoside-5'-triphosphates, such as two or more of dATP, dCTP, dGTP, dTTP and dUTP. Analogues such as dITP and 7-deaza-dGTP are also useful. Preferably, the four common triphosphates (dATP, dCTP, dGTP and dTTP) are used together.

The PCR reagents described herein are provided and used in PCR in suitable concentrations to provide amplification of the target nucleic acid. The minimal amounts of primers, DNA polymerase, cofactors and deoxyribonucleoside-5'-triphosphates needed for amplification and suitable ranges of each are well known in the art. The minimal amount of DNA polymerase is generally at least about 0.5 units/100 $\mu$l of solution, with from about 2 to about 25 units/100 $\mu$l of solution being preferred, and from about 7 to about 20 units/100 $\mu$l of solution being more preferred. Other amounts may be useful for given amplification systems. A "unit" is defined herein as the amount of enzyme activity required to incorporate 10 nmoles of total nucleotides (dNTP's) into an extending nucleic acid chain in 30 minutes at 74° C. The minimal amount of primer is at least about 0.075 $\mu$molar with from about 0.1 to about 2 $\mu$molar being preferred, but other amounts are well known in the art. The cofactor is generally present in an amount of from about 2 to about 15 mmolar. The amount of each dNTP is generally from about 0.25 to about 3.5 mmolar.

The PCR reagents can be supplied individually, or in various combinations, or all in a buffered solution having a pH in the range of from about 7 to about 9, using any suitable buffer, many of which are known in the art.

Other reagents that can be used in PCR include, for example, antibodies specific for the thermostable DNA polymerase, exonucleases and/or glycosylases. Antibodies can be used to inhibit the polymerase prior to amplification. Antibodies useful in the present invention are specific for the thermostable DNA polymerase, inhibit the enzymatic activity of the DNA polymerase at temperatures below about 50° C., and are deactivated at higher temperatures. Useful antibodies include, monoclonal antibodies, polyclonal antibodies and antibody fragments. Preferably, the antibody is monoclonal. The antibodies useful in the present invention can be prepared using known methods such as those described in Harlow et al., *Antibodies: A Laboratory Manual,* Cold Spring Harbor, N.Y. (1988).

Representative monoclonal antibodies are described in U.S. Pat. No. 5,338,671 (Scalice et al.), the contents of which are hereby incorporated by reference. Two such monoclonal antibodies are readily obtained by a skilled artisan using conventional procedures, and starting materials including either of hybridoma cell lines HB 11126 or 11127, deposited with the American Type Culture Collection (ATCC) (Rockville, Md.). The monoclonal antibody is present in an amount of from about 5:1 to about 500:1 molar ratio to the DNA polymerase.

Antibodies specific to the thermostable DNA polymerase can be used in the present invention alone or in combination with an exonuclease and/or a glycosylase as described in U.S. application Ser. No. 08/385,019, filed Feb. 7, 1995, now abandoned by Sutherland et al., titled "Use of Exonuclease and/or Glycosylase as Supplements to Anti-Polymerase Antibody to Increase Specificity in Polymerase Chain Reaction". The combined use of an antibody, an exonuclease and a glycosylase reduces the formation of zero cycle artifacts. Suitable exonucleases for use in PCR include, but are not limited to, exonuclease III, exonuclease I, exonuclease, T7 exonuclease, ribonuclease II, polynucleotide phosphorylase and BAL 31 nuclease. Such exonucleases are commercially available or can be obtained by methods known in the art. Glycosylases useful in the present invention are those that specifically cleave unconventional bases, i.e., bases other than A, G, C, or T in DNA and A, G, C, and U in RNA. Preferred glycosylases include uracil-N-glycosylase (UNG), hypoxanthine-DNA glycosylase and 3-methyadenine-DNA glycosylases I and II. In a preferred embodiment, Taq polymerase, a monoclonal antibody against Taq polymerase, exonuclease III and uracil-N-glycosylase are employed.

A target nucleic acid (either DNA or RNA) can be obtained from any of a variety of sources as noted above. Generally, the sample is treated in some manner to make the DNA available for contact with the primers and other PCR reagents. This usually means removing unwanted proteins and cellular matter from the sample using one of the various procedures known in the art.

Since the nucleic acid to be amplified and detected is often in double stranded form, the two strands must be separated (that is, denatured) before priming and amplification can take place. Denaturation can be accomplished using a heat treatment alone or in combination with any other suitable physical, chemical or enzymatic means for separating the strands as described in the art. Initial denaturation is generally carried out by heating the sample suspected of containing the target nucleic acid at a first temperature of from about 85° to about 100° C. for a suitable time, for example, from about 1 second to 3 minutes.

The denatured strands are then cooled to a temperature which is generally in the range of from about 55° to about 70° C. for priming of the strands. The time needed for cooling the strands after the initial denaturation will vary depending upon the type of apparatus used for the PCR process.

Once the denatured strands are cooled to the second temperature, the denatured strands are incubated together with the reaction mixture containing PCR reagents at a suitable temperature to effect annealing (hybridization) of the primers to the strands and extension of the primers to form primer extension products. Generally, this temperature is at least about 50° C., and preferably in the range of from about 62° to about 75° C. The time for incubation can vary widely depending upon the incubation temperature and the length of extension products desired, but in preferred embodiments, it is from about 1 to about 120 seconds. Each cycle of PCR can be carried out using either two or three different temperatures, one for denaturation, and a second or third temperature for priming and/or primer extension product formation.

At any point after the generation of at least one primer extension product, amplification can be stopped and the target primer extension product (the "amplified" target) detected. However, if the hybridized primer extension products are then denatured, PCR can be carried out further in as many cycles of priming, extending, and denaturing as desired. The number of PCR cycles carried out will depend, in part, upon the amount of amplified target desired and can be readily determined by those skilled in the art. Generally, at least 20 cycles will be carried out, with from 20 to 50 cycles being preferred.

When amplifying multiple target nucleic acids, especially instances where one of the targets is a lower copy number target and one is a high copy number target, a secondary renaturation step can be employed after primary PCR cycles have been carried out, as described in U.S. application Ser. No. 08/264,102, filed Jun. 6, 1994, to Backus et al., titled "Method of Amplification Using Intermediate Renaturation Step." After at least 15 primary amplification cycles (a primary amplification cycle comprising denaturation, priming and extension), secondary amplification cycles are carried out having the same steps, except that a renaturation step is included after each denaturation step and before primer annealing. Renaturation is accomplished by cooling the reaction mixture to a fourth temperature as described in U.S. application Ser. No. 08/264,102 now U.S. Pat. No. 5,559,013.

In the present invention, after the target nucleic acid is amplified using the desired number of PCR cycles, a post amplification, pre-detection incubation step is performed to inactivate the DNA polymerase and, thereby, increase detection sensitivity. The conditions under which the post amplification incubation step is carried out will depend upon the thermostable enzyme employed but the combined temperature and incubation period will be such as to inactivate the enzyme. Preferably, this post amplification incubation step is carried out by incubating the PCR amplification mixture containing the amplified target at a temperature of between about 95° C. and about 120° C. for between about 1 second and about 30 minutes. Preferably, the post amplification incubation step involves heating at a temperature of between 100° C. and 110° C. for 15 seconds to 10 minutes, more preferably at a temperature of about 105° C. for up to 5 minutes.

Amplification, including the post amplification, pre-detection incubation step, is preferably conducted in a continuous, automated manner so that the reaction mixture is temperature cycled in a controlled manner for desired preset times. A number of instruments have been developed for this purpose and are available to those skilled in the art. Preferably, amplification and the post amplification incubation step are carried out in a closed reaction vessel, such as the chemical test pack described in U.S. Pat. No. 5,229,297, which vessel is processed on the instrument described in U.S. Pat. No. 5,089,233.

Once the post amplification incubation has been performed, the amplified nucleic acid targets can be detected. Detection can be accomplished in a number of known ways, such as those described in U.S. Pat. No. 4,965,188 (Gelfand et al.). For example, the amplified nucleic acids can be detected using Southern blotting, dot blot techniques, or nonisotopic oligonucleotide capture detection with a labeled probe. Alternatively, amplification can be carried out using primers that are appropriately labeled, and the amplified primer extension products can be detected using procedures and equipment for detection of the label.

In a preferred embodiment, the amplified target nucleic acid is detected using an oligonucleotide probe that is labeled for detection and can be directly or indirectly hybridized with the amplified target. The probe may be soluble or attached to a solid support. In another preferred embodiment, one or more of the primers used to amplify the target nucleic acid is labeled, for example, with a specific binding moiety. The resulting primer extension product into which the labeled primer has been incorporated can be captured with a probe. Detection of the amplified target hybridized to the probe can be achieved by detecting the presence of the labeled probe or labeled amplified target using suitable detection equipment and procedures that are well known in the art. Certain labels may be visible to the eye without the use of detection equipment.

In a more preferred embodiment, one or more of the primers used to amplify the target nucleic acid is labeled with biotin and the biotinylated amplified target nucleic acids are hybridized to probes attached to a solid support. The bound targets are then detected by contacting them with a streptavidin-peroxidase conjugate in the presence of an oxidant, such as hydrogen peroxide, and a suitable dye-forming composition. For example, useful dye-providing reagents include tetramethylbenzidine and derivatives thereof, and leuco dyes, such as triarylimidazole leuco dyes as described in U.S. Pat. No. 4,089,747 (Bruschi).

Preferably, amplification, the post amplification, pre-detection incubation step and detection are all carried out in a closed reaction vessel to reduce the risk of contamination. Using a closed reaction vessel as described in U.S. Pat. No. 5,229,297, a sample can be amplification, incubated and detected without opening up the reaction vessel during the process, thereby minimizing the risk of contamination.

As used herein, when in reference to time the term "about" refers to ±10% of that time limit. When used in reference to temperatures, the term "about" refers to ±5° C.

The following examples are included to illustrate the practice of this invention, and are not meant to be limiting in any way. All percentages are by weight unless otherwise indicated.

EXAMPLES

Materials

Recombinant DNA polymerase from *Thermus aquaticus* was prepared using, known procedures, such as that described in EP-A-0 482 714, and had an activity of about 250,000 units/mg of protein.

The primers used in the following Examples had the following sequences:

5'-CACCACGCAGCGGCCCTTGATGTTT-3' (SEQ. ID NO. 1),

5'-TGCACTGCCAGGTGCTTCGGCTCAT-3' (SEQ. ID NO. 2.)

The capture probe has the following sequence:

5'-GAACCGAGGGCCGGCTCACCTCTATGTTGG-3' (SEQ. ID NO. 3).

The primers and probes used in the following Examples were prepared using known starting materials and procedures using an Applied Biosystems Model 380B, three column DNA synthesizer using standard phosphoramidite chemistry and the ABI 1$\mu$ molar scale, fast cycle protocol. Nucleoside-3'-phosphoramidites and nucleoside derivatized controlled pore glass supports were obtained from Applied Biosystems. The primers had the sequences identified above. They were functionalized at the 5' end with two amino tetraethylene glycol spacers according to U.S. Pat. No. 4,962,029, followed by a single commercially available DuPont biotin phosphoramidite. The probes were functionalized at the 3' end with two tetraethylene glycol spacers followed by a single aminodiol linking group according to U.S. Pat. No. 4,914,210. All purifications were carried out using a nucleic acid purification column, followed by reverse phase HPLC techniques. Deoxyribonucleotides (dNTP's) were obtained from Sigma Chemical Co.

A streptavidin-peroxidase conjugate solution was used that comprised a commercially available (Sigma Chemical Co.) conjugate of steptavidin and horseradish peroxidase, casein (0.5%), and merthiolate (0.5%) in a phosphate buffered saline solution (24 mmolar sodium phosphate and 75 mmolar sodium chloride). 10 mmolar 4'-hydroxyacetanilide was added as a conjugate stabilizer. In Examples 1 and 2 the final conjugate concentration was 1.1 nM. In Example 3 the final conjugate concentration was 0.28 nM.

Cytomegalovirus, strain AD 169 DNA was received from Applied Biotechnology Inc. Briefly, the DNA was extracted from human foreskin fibroblast cell lines using conventional procedures:

| Virus Lot Specifications | |
|---|---|
| Virus: | Cytomegalovirus, strain AD 169 |
| Cell Line for propagation: | Human Foreskin Fibroblasts |
| Virus Preparation: | Sucrose density gradient purified, 1000x concentration |
| Virus Particle Count: | $1.65 \times 10^{10}$ vp/mL at 1000x |
| $TCID_{50}$ Titre on Active Virus: | $10^7$ $TCID_{50}$ units/mL at 1000x |
| DNA Extract Specifications | |
| Volume: | 0.1 mL |
| Suspending Buffer: | 10 mM Tris/ 1mM EDTA, pH 8.0 |
| Extract Preparation: | SDS, proteinase K digestion followed by phenol/chloroform extraction and ethanol precipitation. One mL of extract prepared from 1 mL of purified virus. |
| Shipping and Storage: | 6 × 0.1 mL shipped frozen at −70° C. Stored at −20° C. or colder. |

The leuco dye dispersion contained agarose (0.5%), 4,5-bis(4-dimethylaminophenyl)-2-(4 hydroxy-3-methoxyphenyl)imidazole leucodye (250 μmolar), diethylenetriamine pentaacetic acid (100 μmolar), 3'-chloro-4¹-hydroxyacetanilide (5 mmolar), polyvinylpyrrolidone (112 mmolar), and sodium phosphate, monobasic, 1-hydrate (10 mmolar) and hydrogen peroxide ($H_2O_2$) (8.82 mmolar).

The wash solution (pH 7.4) contained sodium chloride (373 mmolar), (ethylenedinitrilo)tetraacetic acid disodium salt (2.5 mmolar), decyl sodium sulfate (38 mmolar) and ethylcerithio salicylic acid, sodium salt (25 μmolar)in sodium phosphate, monobasic 1-hydrate buffer (25 mmolar).

Monoclonal antibodies were used in the reaction mixture. These antibodies "TP1-12.2" and TP4-9.2"are specific to DNA polymerase from *Thermus acquaticus* and are described in more detail in U.S. application Ser. No. 08/385, 019, filed Feb. 7, 1995, by Sutherland et al., titled "Use of Exonuclease and/or Glycosylase as Supplements to Anti-Polymerase Antibody to Increase Specificity in Polymerase Chain Reaction".

The polymerase chain reaction mixture (75 uL) contained tris(hydroxymethyl)aminomethane buffer (10 mmolar, pH 8), potassium chloride (50 mmolar), magnesium chloride (4 mmolar), dATP, dCTP, dGTP, and dTTP (0.3 mM each), 0.00–0.75 mM EDTA, the primers SEQ ID NO: 1 and SEQ ID NO: 2 (0.4 μmolar each), Type IV gelatin (100 mg/mL), Taq polymerase (16 units/100 μl), and glycerol (9.5%). A fifty fold molar excess (over polymerase) of TP1-12.2 and a 5× excess of TP4-9.2 were used.

Unless otherwise indicated, PCR amplification was carried out using the Perkin-Elmer GeneAmp PCR System 9600 thermocycler.

To form capture reagents, the probes were covalently attached to polymeric particles (1 μm average diameter) prepared using conventional emulsion polymerization techniques, from poly[styrene-co-3(p-vinyl-benzylthio) propionic acid](95:5 weight ratio, 1 μm average diameter). A suspension of the particles in water was washed with 2-(N-morpholino)ethanesulfonic acid buffer (0.1 molar, pH6), and suspended to about 10% solids. A sample (3.3 ml) of the washed particles, diluted to 3.33% solids in the buffer (0.1 molar, was mixed with 1-(3-dimethylaminopropyl)-3-ethylcarbodiimide hydrochloride (2.1 ml of 84 mg/ml water) and the probe 983 μl of 44.44 OD/ml nanopure water). The resulting suspension was heated at 50° C. in a water bath for about two hours with intermittent mixing and centrifuged. The particles were then washed three times with tris (hydroxymethyl)aminomethane buffer (0.01 molar, pH 8) containing (ethylenedinitrilo)tetraacetic acid disodium salt (0.001 molar) and resuspended therein to 4% solids. The particles were then immobilized in discrete spots in A Johnson & Johnson Clinical Diagnostic's PCR pouch at 2% solids plus glue. The PCR products were detected using the A Johnson & Johnson Clinical Diagnostic's Pouch detection system.

Other reagents and materials were obtained either from commercial sources or prepared using readily available starting materials and conventional procedures.

Post Amplification Incubation Step Prior to Product Detection for Increased Detection Sensitivity Example 1

This example demonstrates the present invention to detect nucleic acid products that have been produced using PCR by employing a post amplification incubation step to denature the polymerase. Positive pools were created by amplifying CMV target (10 to 10,000 copies CMV target per 75 μl of reaction volume) using 30–45 cycles of the following PCR protocol:

1. Denaturation by heating at 95° C. for 15 seconds, and
2. Cycles of priming and extending at 70° C. for 30 seconds.

Product concentration was quantified by gel electrophoresis with known concentrations of DNA standards. The resulting post amplification PCR reaction mixture was then used as described below.

In addition to generating the post-PCR reaction mixture, a CMV negative product pool was prepared by carrying out PCR amplification on the PCR reaction mixture absent the addition of CMV DNA target using the above PCR protocol.

The post amplification PCR reaction mixture ($10^{-7}$ to $10^{-8}$M) was diluted 1:100 to 1:5000 with CMV negative product pool to obtain a final CMV DNA concentration of $1 \times 10^{-10}$ M, $2.5 \times 10^{-11}$ M, or $5 \times 10^{-11}$ M. The diluted post amplification PCR reaction mixture (85 μl post-amplification sample loaded per pouch with an assumed volume of 75 ul reaching the amplification compartment) was then subjected to a post amplification incubation to deactivate the polymerase. The post-amplification incubation step was carried out for 2 minutes at 97° C. or 100° C., or for 5 minutes at 100° C.

After the post amplification incubation, the amplified product was detected by capturing the target nucleic acids with the capture reagents at 58° C. for 5 minutes inside a Johnson & Johnson Clinical Diagnostic's PCR pouch. Each pouch contained the dry equivalent of 2 ul of beads per discrete spot. The volume of all detection fluids was 200 ul per PCR pouch. The captured products were then contacted and incubated with the streptavidin-peroxidase conjugate solution at 55° C. for 1 minute. A wash was carried out using the wash solution for 1 minute at 55° C., after which the dye-providing composition was added and allowed to incubate for 4 minutes at 40° C. The resulting signal was read with a line array scanner. The scanner determined the change in reflectance density ($\Delta$Dr). $\Delta$Dr is the difference in the reflectance density between an initial reading before initiation of dye development and a final reading taken after 4 minutes of dye development. The scanner background on visually negative capture beads ranged from 0.05 to 0.1 Dr units.

The following results show that a post amplification incubation step increases detection sensitivity:

| Post amplification Incubation Condition | Product Concentration | CMV _Dr (Scanner) |
|---|---|---|
| 2 min at 97° C. | $1 \times 10^{-10}$ M | 0.175 |
| " | $5 \times 10^{-11}$ M | 0.14 |
| " | $2.5 \times 10^{-11}$ M | 0.11 |
| 2 min at 100° C. | $1 \times 10^{-10}$ M | 0.265 |
| " | $5 \times 10^{-11}$ M | 0.19 |
| " | $2.5 \times 10^{-11}$ M | 0.13 |
| 5 min at 100° C. | $1 \times 10^{-10}$ M | 0.435 |
| " | $5 \times 10^{-11}$ M | 0.31 |
| " | $2.5 \times 10^{-11}$ M | 0.21 |

These results show that a 5 minute post amplification incubation step at 100° C. increases the effective detection limit above background by at least four-fold and probably by at least five-fold. Based on these results, especially the improvement by increasing the incubation period at 100° C. from 2 minutes to 5 minutes, a second experiment was carried out with a 15 minute post amplification incubation at 100° C.

Example 2

In this second experiment, amplification of CMV DNA was carried out as described in Example 1. The resulting post amplification PCR reaction mixture was diluted with a CMV negative product pool and subjected to a post amplification incubation to inactivate the polymerase as described in Example 1. The post-amplification incubation step was carried out for 15 minutes at 100° C. After the post amplification incubation, the amplified product was detected as described in Example 1.

The following results show that a post amplification incubation step increases detection sensitivity:

| Post amplification Incubation Condition | Product Concentration | CMV _Dr (Scanner) |
|---|---|---|
| 2 min at 97° C. | $1 \times 10^{-10}$ M | 0.140 |
| " | $1 \times 10^{-10}$ M | 0.122 |
| 5 min at 100° C. | $1 \times 10^{-10}$ M | 0.336 |
| " | $1 \times 10^{-10}$ M | 0.346 |
| 15 min at 100° C. | $1 \times 10^{-10}$ M | 0.503 |
| " | $1 \times 10^{-10}$ M | 0.480 |

These results suggest that increasing the post amplification incubation time at 100° C. gains additional benefits.

Example 3

To determine whether an additional detection sensitivity benefit could be realized by increasing the incubation temperature, amplification of CMV DNA was carried out as described in Example 1 and subjected post amplification incubation at 100° C. or 103° C. Various incubation times at 103° C. were investigated. In addition, this experiment was carried out with a less sensitive detection chemistry that has a final conjugate concentration of 0.28 nM. The results of this experiment were:

| Post Amplification Incubation Condition | Product Concentration | CMV _Dr (Scanner) |
|---|---|---|
| 5 min at 100° C. | $1 \times 10^{-10}$ M | 0.152 |
| 15 min at 100° C. | $1 \times 10^{-10}$ M | 0.270 |
| 2 min at 103° C. | $1 \times 10^{-10}$ M | 0.264 |
| 5 min at 103° C. | $1 \times 10^{-10}$ M | 0.318 |

These results demonstrate that at least an additional two-fold increase, and probably a three-fold increase, can be attained by increasing the post amplification incubation step temperature from 100° C. to 103° C. and maintaining the five minute incubation period.

Example 4

This example demonstrates how the present invention, a post amplification heat step to kill thermostable amplification enzymes, can be utilized to increase detection sensitivity in an enclosed amplification and detection vessel. In this example, target nucleic acids are amplified, subjected to post amplification incubation, and detected in the absence of a step that opens the reaction vessel and exposes its contents to the environment. While the example demonstrate the use of the invention in the Johnson & Johnson Clinical Diagnostics' PCR Pouch, the invention would also apply to other containment amplification and detection vessels.

Samples (positive, negative or unknown) are mixed with master mix containing components required for efficient PCR amplification, including Taq polymerase, buffer, dNTP's, salts of monovalent and divalent cations, primers and anti-Taq antibodies, if desired, such that the final concentrations are suitable for amplification. A desirable example for reaction conditions is described in the Methods and Materials section above. The resulting mixture is then loaded into the amplification compartment of a Johnson & Johnson Clinical Diagnostics' PCR pouch and enclosed amplification and detection is carried out. Amplification is carried out using an automated PCR processor described in U.S. Pat. No. 5,089,233 under the following conditions:

Denaturation of nucleic acid target and anti-Taq antibodies by heating to 95° C. for 3 minutes followed by 40 cycles of amplification consisting of:

1. Denaturation of target by heating at 96° C. for 5 seconds; and
2. Priming the target with target-specific oligonucleotide primers and subsequent extension of the primers with polymerase by heating at 70° C. for 40 seconds.

After amplification is complete, a post amplification, pre-detection incubated heat step is carried out by heating the sample in the pouch to 103° C. for 5 minutes. This step is performed without opening the PCR pouch and exposing its contents to the outside environment. This step denatures the amplification enzymes and the amplification products. Following this post-amplification heat step, amplification products are delivered to the detection compartment of the PCR Pouch by a roller mechanism and amplification products are captured by specific oligonucleotide probes covalently attached to 1 micron latex particles, which are dried down in discrete locations in the detection area. Hybridization between the biotinylated amplification products and the specific capture probes is carried out for 5 minutes at 58° C. The captured products are then contacted and incubated with the streptavidin-peroxidase conjugate solution at 55° C. for 1 minute. A wash step is carried out using a wash solution (described above) for 1 minute at 55° C., after which the dye-providing composition (described above) is added and allowed to incubate for 4 minutes at 40° C. The resulting signal is read with a line array scanner. Determination of positivity and negativity is made for each individual sample by comparing the signal with previously set positive and negative cut-off values utilizing a previously determined algorithm.

In samples that would give very low positive signals or borderline signals, the detection signals should be higher for samples that have undergone a 5 minute, 103° C. denaturation step relative to controls which have undergone a 2 minute, 97° C. denaturation step, which completely denature the amplification products, but does not completely thermally denature the Taq polymerase.

All publications mentioned hereinabove are hereby incorporated by reference.

While the foregoing invention has been described in some detail for purposes of clarity and understanding, it will be appreciated by those skilled in the art from a reading of this disclosure that various changes in form and detail can be made without departing from the true scope of the invention.

What is claimed:

1. A method of inactivating a thermostable amplification enzyme in a method for amplifying and detecting a target nucleic acid in a closed reaction vessel comprising:

a) contacting a sample suspected of containing said target nucleic acid with at least two oligonucleotides and a thermostable amplification enzyme, wherein said oligonucleotides are substantially complementary to a portion of said target nucleic acid, under conditions such that said target nucleic acid is amplifiable;

b) amplifying said target nucleic acid;

c) denaturing amplified target nucleic acids to form single stranded nucleic acids;

d) after the denaturation step and prior to detection, inactivating the thermostable amplification enzyme by incubating said sample for between 2 minutes and 30 minutes at between 97° C. and 120° C.; and e) detecting the presence or absence of the amplified target nucleic acids, wherein the reaction vessel remains closed during steps (a) through (e), and wherein the inactivating step results in an increase in detection sensitivity over background as compared to the detection sensitivity without the inactivating step.

2. The method according to claim 1, wherein four oligonucleotides and a thermostable DNA ligase are used.

3. A method of inactivating a thermostable amplification enzyme in a method for amplifying and detecting a target nucleic acid in a closed reaction vessel comprising:

a) contacting a sample suspected of containing said target nucleic acid with four different nucleoside triphosphates, a thermostable DNA polymerase, and two primers, wherein said primers are substantially complementary to said target nucleic acid, under conditions such that said target nucleic acid is amplifiable:

b) amplifying said target nucleic acid;

c) denaturing amplified target nucleic acids to form single stranded nucleic acids;

d) after the denaturation step and prior to detection, inactivating the thermostable amplification enzyme by incubating said sample for between 2 minutes and 30 minutes at between 97° C. and 120° C.; and e) detecting the presence or absence of the amplified target nucleic acids, wherein the reaction vessel remains closed during steps (a) through (e), and wherein the inactivating step results in an increase in detection sensitivity over background as compared to the detection sensitivity without the inactivating step.

4. The method according to claim 3, wherein said post amplification incubation step is carried out for between 2 minutes to 10 minutes at between 100° C. to 110° C.

5. The method according to claim 3, wherein said post amplification incubation step is carried out for between 2 minutes to 5 minutes at about 103° C.

6. The method of claim 3, wherein said target nucleic acid is DNA or RNA.

7. The method of claim 6, wherein said target nucleic acid is DNA.

8. The method of claim 6, wherein said target nucleic acid is RNA.

9. The method of claim 3, wherein said nucleoside triphosphates are deoxyribonucleoside triphosphates.

10. The method of claim 9, wherein said deoxyribonucleoside triphosphates are dATP, dCTP, dGTP, and dTTP.

11. The method of claim 3, wherein said thermostable DNA polymerase is selected from the group consisting of thermus aquaticus polymerase, *therimus thermophilus* polymerase, and *Thermococcus litoralis* polymerase.

12. The method of claim 3, wherein at least one of said primers is labeled.

13. The method of claim 3, wherein said primers are labeled.

14. The method of claim 12, wherein at least one of said primers is labeled with a specific binding ligand.

15. The method of claim 14, wherein said specific binding ligand is biotin.

16. The method of claim 3, wherein said amplified target nucleic acids are detected using a labeled probe that can hybridize with one of the one or more target nucleic acids.

17. The method of claim 16, wherein said labeled probe is attached to a solid support.

18. The method of claim 3, wherein at least one of said primers are labeled with a specific binding moiety and said amplified target nucleic acids are detected using a probe that can hybridize with one of the one or more target nucleic acids.

19. The method of claim 18, wherein said probe is attached to a solid support.

20. A method of inactivating a thermostable amplification enzyme in a method for amplifying and detecting a target nucleic acid in a closed reaction vessel comprising:

a) contacting a sample suspected of containing said target nucleic acid with four different nucleoside triphosphates, a thermostable DNA polymerase, and two primers, wherein at least one of said primers is labeled with biotin and said primers are substantially complementary to said target nucleic acid, under conditions such that said target nucleic acid is amplifiable.

b) amplifying said target nucleic acid, c) denaturing, amplified target nucleic acids to form single stranded nucleic acids;

d) after the denaturation step and prior to detection, inactivating the thermostable amplification enzyme by incubating said sample for between 2 minutes and 5 minutes at about 103° C.; and e) detecting(the presence or absence of the biotinylated amplified target nucleic acids by reacting the biotinylated amplified target nucleic acids with an avidin-enzyme conjugate, followed by reaction of the enzyme with a substrate reagent to produce a detectable colorimetric or chemiluminescent signal, wherein the reaction vessel remains closed during steps (a) through (e).

21. The method of claim 20, wherein said biotinylated amplified target nucleic acids are detected by contacting them with an avidin-peroxidase conjugate, followed by reaction of peroxidase, in the presence of an oxidant, with either: luminol to produce a detectable chemiluminescent signal, or a leuco dye to produce a detectable calorimetric signal.

\* \* \* \* \*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

CACCACGCAG CGGCCCTTGA TGTTT                                                25

(2) INFORMATION FOR SEQ ID NO:2:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

TGCACTGCCA GGTGCTTCGG CTCAT                                                25

(2) INFORMATION FOR SEQ ID NO:3:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

GAACCGAGGG CCGGCTCACC TCTATGTTGG                                           30